(12) United States Patent
Kim

(10) Patent No.: US 8,715,162 B2
(45) Date of Patent: May 6, 2014

(54) METHOD FOR COMPLEX PHALOPLASTY USING CIRCUMCISED FORESKIN AS AUTOGRAFT

(76) Inventor: Joon-Yong Kim, Seoul (KR)

(*) Notice: Subject to any disclaimer, the term of this patent is extended or adjusted under 35 U.S.C. 154(b) by 100 days.

(21) Appl. No.: 13/552,019

(22) Filed: Jul. 18, 2012

(65) Prior Publication Data
US 2014/0024888 A1    Jan. 23, 2014

(51) Int. Cl.
*A61F 5/00* (2006.01)

(52) U.S. Cl.
USPC .................................................. 600/38

(58) Field of Classification Search
CPC ................................ A61B 19/00; A61F 5/00
USPC .............................. 128/897–898; 600/38–41
See application file for complete search history.

(56) References Cited

U.S. PATENT DOCUMENTS

| | | | |
|---|---|---|---|
| 6,173,714 B1 * | 1/2001 | Cho | 128/898 |
| 6,418,934 B1 | 7/2002 | Chin | |
| 6,582,356 B2 * | 6/2003 | Kim | 600/40 |
| 7,584,757 B2 | 9/2009 | Krakovsky | |

* cited by examiner

*Primary Examiner* — Samuel Gilbert
(74) *Attorney, Agent, or Firm* — Nath, Goldberg & Meyer; Tanya E. Harkins

(57) ABSTRACT

Disclosed is a method for complex phalloplasty for widening a penis, using a circumcised foreskin as an autologous graft. In the method, a foreskin cut off by circumcision, conventionally discarded as waste, is implanted as an autograft in phalloplasty, whereby the penis can be widened.

5 Claims, 6 Drawing Sheets

METHOD FOR COMPLEX PHALOPLASTY USING CIRCUMCISED FORESKIN AS AUTOGRAFT

BACKGROUND OF THE INVENTION

1. Field of the Invention

The present invention relates to a method for complex phalloplasty for widening a penis, using a circumcised foreskin as an autologous graft. More particularly, the present invention relates to a novel method for complex phalloplasty in which a foreskin cut off by circumcision, conventionally discarded as waste, is implanted as an autograft in phalloplasty, whereby the penis can be widened.

2. Description of the Related Art

Male circumcision is the most ancient and most widely been performed artificial modification of the penis by surgery. Often, the histological and cultural backgrounds of circumcision vary from one region to another. From the point of view of social customs, for instance, circumcision is considered as a rite of passage marking a boy's entrance into adulthood. In some countries, circumcision is performed for religious reasons.

To date, medical reasons including the prophylaxis of penile diseases account for most circumcisions, which is often done in the infancy. In a phimosis condition where the foreskin cannot be fully retracted over the glans penis, unsanitary substances such as smegma accumulate, giving rise to an unpleasant odor, pain and disease such as posthitis, balanitis, balanitis xerotica obliterans, balanoposthitis and urinary tract infections. In addition, several types of research have documented that male circumcision significantly reduces the risk of HIV infection in heterosexual men. Moreover, a buried penis may appear somewhat immature and reduce sexual attraction because the glans penis, which is regarded as a male symbol, is not seen. Because only a small amount of further extension is possible before the elastic band breaks, the penis may remain underdeveloped if not circumcised.

Medically, there are various methods for performing circumcision.

In most of them, the prepuce and subcutaneous tissue is cut off to the extent that the glans penis is exposed. That is, the end of the penile skin is withdrawn toward the proximal penis.

Even though it is difficult to medically determine the optimal timing of circumcision, it is commonly performed just after birth, or between birth and the early twenties. Sometimes, some adult men may undergo circumcision and phalloplasty at the same time.

The present inventor has documented the following complaints or inconveniences in association with circumcision.

First, the penis is shortened or thinned because of the removal of too much penile skin or subcutaneous tissue, which typically occurs due to the misjudgment or unskilled surgical techniques of the operator. In this case, the patient may have an inferiority complex about the male genital organ or may feel uncomfortable in his sexual life because the tightened skin causes various problems with erection including pain, the shift of pubic hairs from the pubis to the penis and the shift of the scrotal skin to the penis. In a severe case, the patient may suffer from sexual dysfunction. Another problem is how to dispose of the foreskin or subcutaneous tissue which is cut off upon circumcision.

Reference may be made to some publications pertaining to phalloplasty.

U.S. Patent Publication No. 2008/0051625 (Feb. 28, 2008) discloses a method of widening a penis by inserting a dermal fat graft between the penile skin and the buck's fascia along the circumference of the penis.

U.S. Patent Publication No. 2006/0096603 (May 11, 2006) discloses a method for complex phalloplasty with minimal incision, comprising minimally incising a part of the penile skin directly behind the glans to expose the Buck's fascia and inserting a penile enhancement object between the subglans margin and the tunica albuginea through the minimally incised penile skin part. Another surgical method for penis enlargement is found in U.S. Pat. No. 7,806,821 (Oct. 5, 2010), "Method of Phalloplasty Using Multiple Slits Tissue or Multiple Pieces Tissue" to the present inventor (Kim, Joon-Yong).

These surgical methods in the prior art are not concerned about penis enlargement and circumcision taken together, but only with the former.

Under the background, the present inventor conceived the use of the circumcised penile skin or subcutaneous tissue in penis enlargement, thus accomplishing circumcision and phalloplasty in a single operation. That is, the prepuce and subcutaneous which is cut off upon circumcision can be used as an autograft for penis enlargement. The use of autografts can overcome the problems generated upon the procurement of allografts or artificial implants such as silicon. For example, allograft or artificial implants are expensive and, when applied to the patient, may cause side effects such as inflammation, graft rejection, foreign body sensation and tissue necrosis. In contrast, the diversion of the prepuce and subcutaneous tissue excised by circumcision into phalloplasty for penis enlargement overcomes the problems encountered in the prior art because it is an autograft. Further, when implanted to the patient, the autograft guarantees better post-surgical recovery than does the allograft or artificial implants.

In this context, circumcision and phalloplasty are performed simultaneously in a single operation so that the prepuce and subcutaneous tissue that is cut off during the circumcision is recycled to be used in phalloplasty for penis enlargement in accordance with the present invention. In addition, the method of the present invention guarantees safety for phalloplasty because the implant is autologous tissue. Moreover, the method of the present invention characterized by the simultaneous performance of circumcision and phalloplasty is advantageous in that the patient experiences post-surgical pain only once and the cost of operation is significantly reduced.

SUMMARY OF THE INVENTION

It is therefore an object of the present invention to provide a novel method for complex phalloplasty which is safe without the side effects caused by the use of allografts or artificial implants.

It is another object of the present invention to provide a novel method for complex phalloplasty which guarantee better post-surgical recovery for the patient.

It is a further object of the present invention to provide a novel method for complex phalloplasty which is economically beneficial for the patient.

In accordance with the present invention, the above objects can be accomplished by providing a method for complex phalloplasty, characterized in that the foreskin and subcutaneous tissue is cut off by circumcision and implanted as an autograft into the penis along the circumference, thereby widening the penis.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1A:
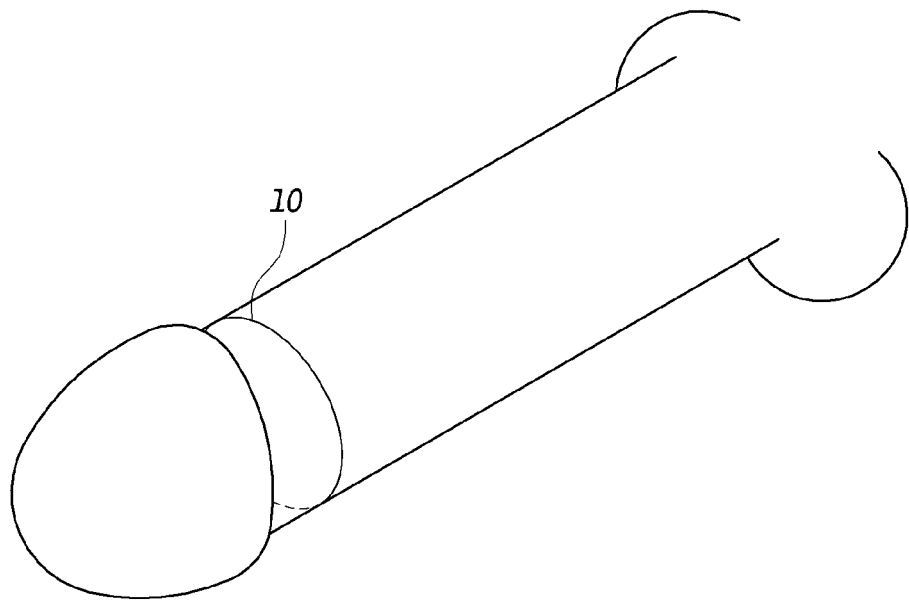
FIGS. 1A to 1E are views illustrating a process of complex phalloplasty for penis enlargement in accordance with the present invention.

Reference now should be made to the drawings, in which the same reference numerals are used throughout the different drawings to designate the same or similar components.

In accordance with an aspect thereof, the present invention provides a method for complex phalloplasty using a circumcised foreskin and subcutaneous tissue as an autograft, comprising:

(i) making a first circumferential incision 10 on penile skin 11 and subcutaneous tissue 12 on the periphery of a distal portion of the penile body;

(ii) making a second circumferential incising 20 the penile skin 11 and subcutaneous tissue 12 on the periphery of a middle portion of the penile body;

(iii) incising a ventral part of the penis in an axial direction between the first and the second circumferential incisions 10-20;

(iv) isolating from the buck's fascia 1 an area of the penile skin 11 and subcutaneous tissue 12 stretching from the ventral central part to a dorsal part;

(v) incising a central dorsal part of the penis to a depth of the subcutaneous tissue from the second incision line toward a proximal root of the penis;

(vi) unfolding the penile subcutaneous tissues from Buck's fascia 1 to form a space in which to insert a graft;

(vii) releasing from the buck's fascia 1 the penile subcutaneous tissue extending from the first circumferential incision 10 to a coronary sulcus to form a space;

(viii) turning the penile skin 11 and subcutaneous tissue 12 released from the Buck's fascia 1 at an angle of 90 degrees;

(ix) implanting the penile skin 11 and subcutaneous tissue 12 into the space between a coronary sulcus and the first circumferential incision 10;

(x) fixing the implant onto the Buck's fascia 1;

(xi) surrounding and covering the implant with the penile skin and subcutaneous tissue of the distal end of the penis; and (xii) suturing the implant to the incised sides and the circumferential incisions, whereby the penis can be enlarged and widened.

Figure 3:
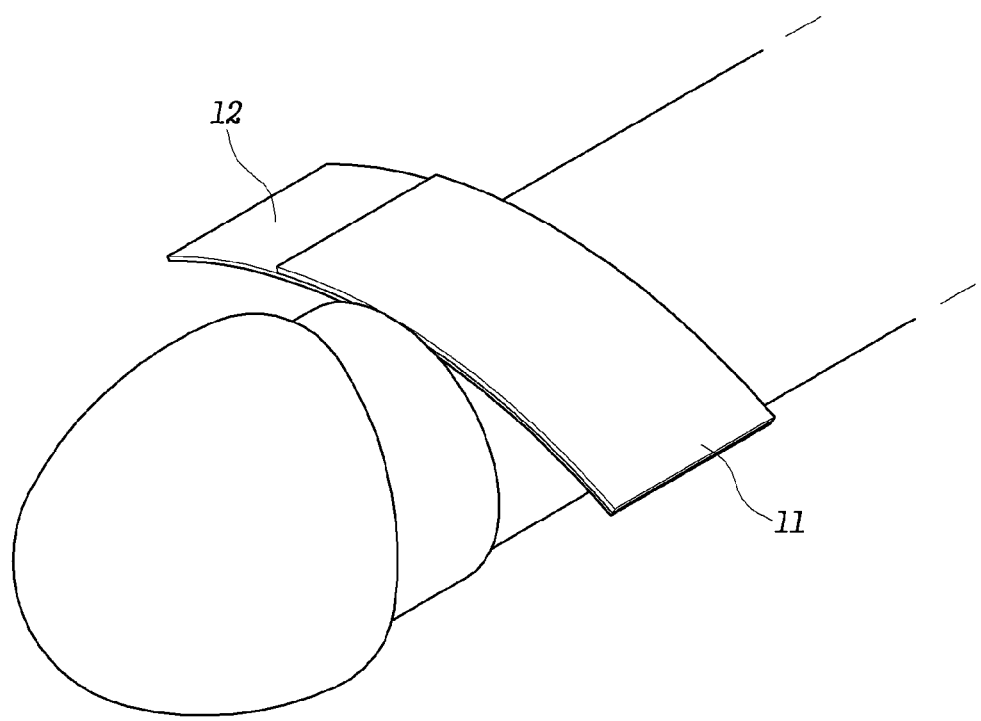
FIG. 3 is a view showing an implant to be applied to a distal portion of the penis: the implant is prepared by separating the penile skin 11 and subcutaneous tissue 12 from the foreskin which is cut off by circumcision.

According to one embodiment of the present invention, the implant is autologous foreskin and the subcutaneous tissue left after circumcision. In a preferred embodiment of the invention, the method for complex phalloplasty using a circumcised foreskin and subcutaneous tissue as an autograft is characterized in that the implant is subcutaneous tissue 12 prepared by isolating the penile skin 11 and subcutaneous tissue 12, as a graft with a width of 1.0~1.5 cm, from a distal end of a penile foreskin tissue to be moved from the penile foreskin tissue on the buck's fascia 1 to a penile end portion, and removing the epidermis and the dermis layer from the graft (FIG. 3).

Figure 4:
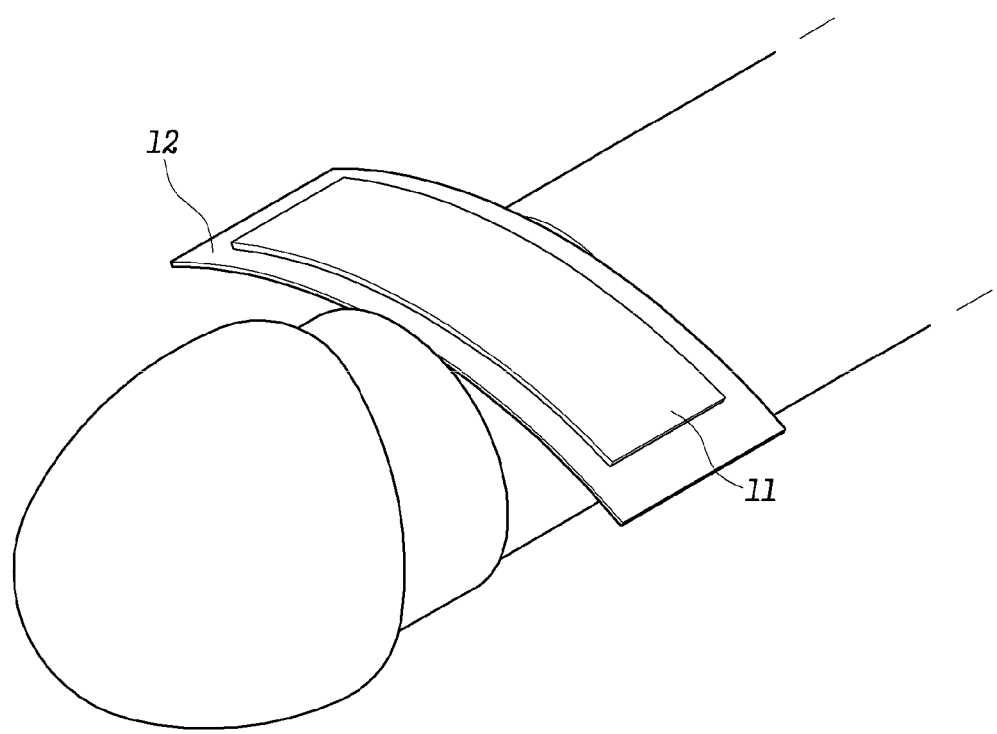
FIG. 4 is a view showing an implant to be sutured to a region of interest: the implant is prepared by separating penile skin 11 and subcutaneous tissue 12 from the foreskin which is cut off by circumcision.

According to another embodiment of the present invention, the method for complex phalloplasty using a circumcised foreskin and subcutaneous tissue as an autograft is characterized in that the implant to be sutured to the incised sides and the circumferential incisions is subcutaneous tissue 12 prepared by isolating the penile skin 11 and subcutaneous tissue 12, as a graft with a width of 0.5~1.0 cm, from an end portion of the foreskin tissue to be moved from the penile foreskin tissue onto the sutured region, and then removing epidermis and dermis layers from the graft, said penile foreskin tissue being isolated from the Buck's fascia 1 of the penile body (FIG. 4).

Figure 5:
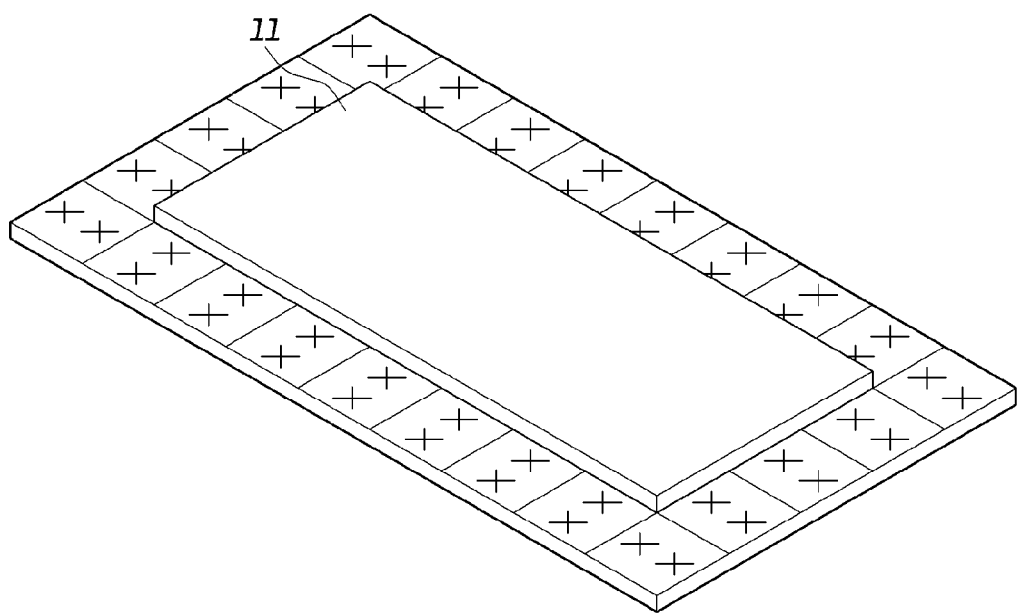
FIG. 5 is a view showing a pattern of slits formed on the implant of the invention.

In one embodiment of the present invention, the method for complex phalloplasty using a circumcised foreskin 11 and subcutaneous tissue 12 as an allograft is characterized in that the implant has a pattern of slits (sheaths) formed thereon (FIG. 5).

A better understanding of the present invention may be obtained from the following examples which are set forth to illustrate, but are not to be construed as limiting the present invention.

Example 1

With reference to FIG. 1, an operating procedure of phalloplasty for widening a penis is illustrated. FIG. 2 is an anatomical view showing the Buck's fascia 1.

Figure 2:
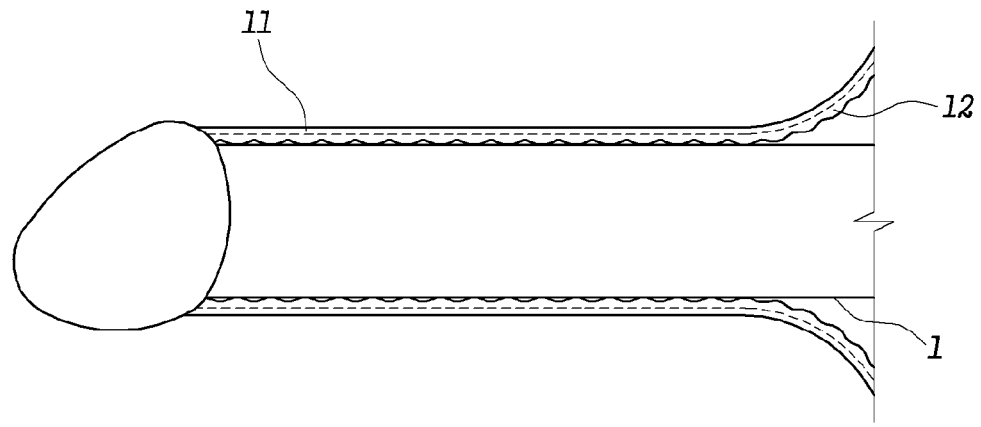
FIG. 2 is a cross-sectional view of a penis showing the penile skin 11 and the subcutaneous tissue 12.

As illustrated in FIG. 1A, a first circumferential incision 10 is performed to cut the penile skin 11 and subcutaneous tissue 12 on the periphery of a distal part of the penis to a depth up to the Buck's fascia 1.

The penis, as depicted in FIG. 2, is divided generally into the erectile tissue and the urethra, both surrounded by the skin layer 11 and the subcutaneous tissue 12. The urethra is encased, together with the inner corpus cavernosum, by Buck's fascia 1. Generally, phalloplasty for penis augmentation is performed in such a manner that an implant is inserted between the Buck's fascia 1 and the subcutaneous tissue 12.

Figure 1B:
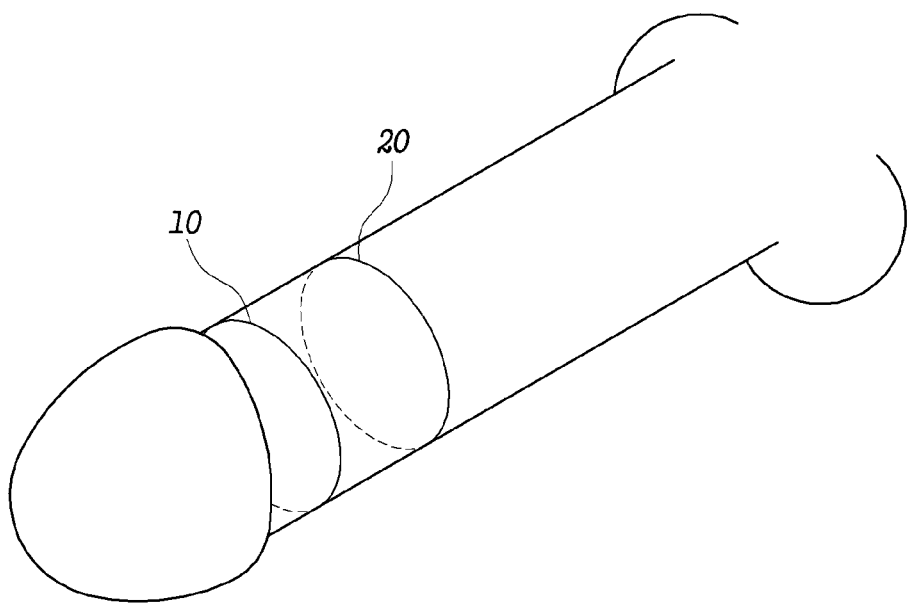

In the present invention, a second circumferential incision 20 is performed to cut the penile skin 11 and the subcutaneous tissue 12 on the periphery of a middle part of the penis to a depth just up to the Buck's fascia 1 (FIG. 1B).

Figure 1C:
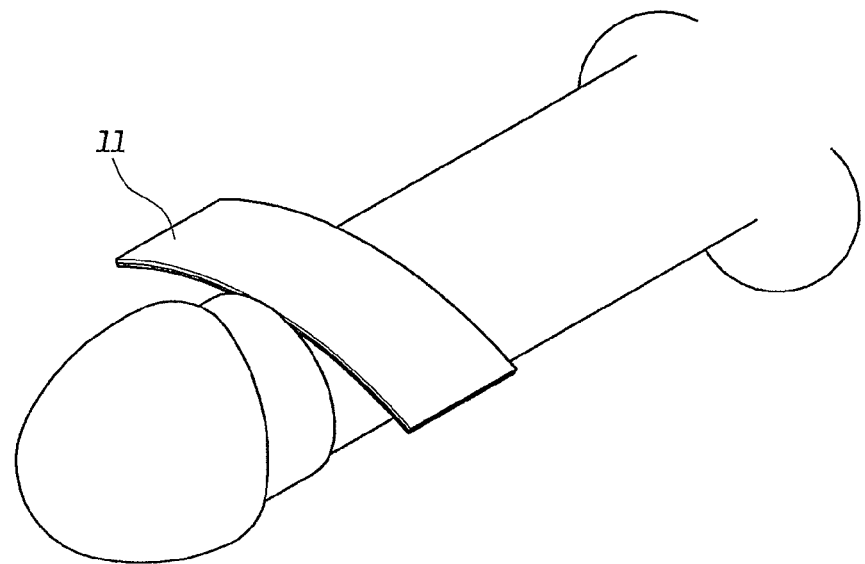

Next, an incision is made on a ventral part of the penis in an axial direction between the two circumferential incisions 10-20 to partially isolate the penile skin 11 and subcutaneous tissue 12 from the Buck's fascia 1 (FIG. 1C).

Figure 1D:
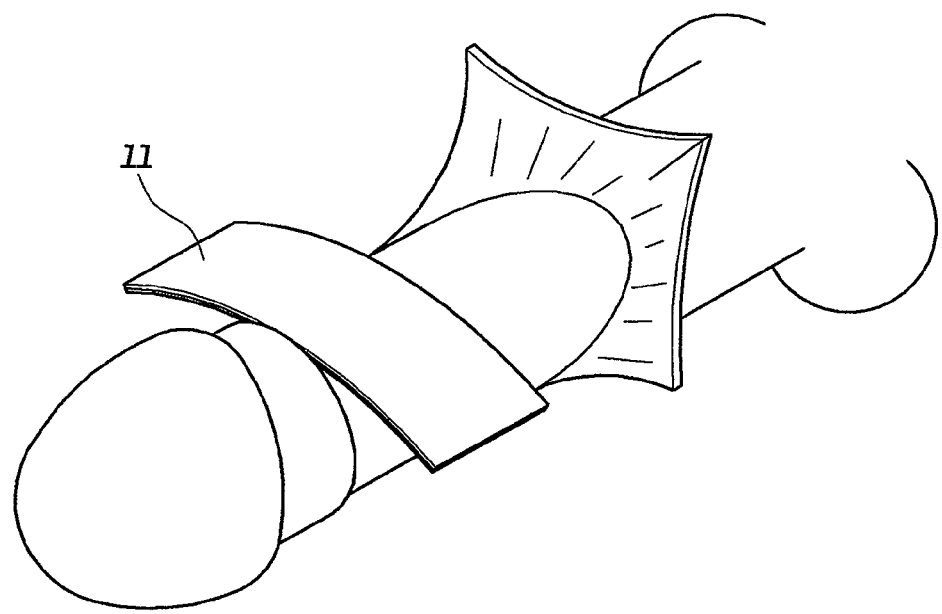
Figure 1E:
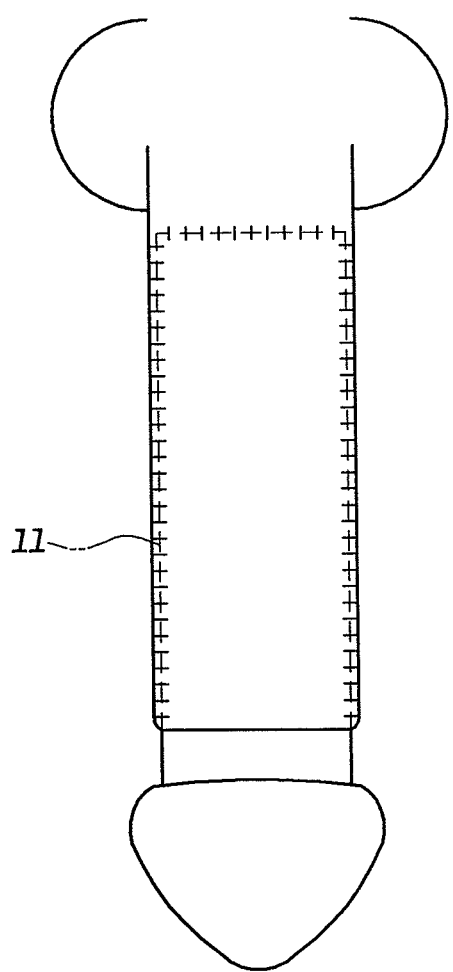

Subsequently, an incision is also made on a central dorsal part of the penis to a depth of the subcutaneous tissue from the second incision line to a proximal part of the penis, followed by separating the subcutaneous tissue 12 from the Buck's fascia 1 to form a space in which to insert a graft (FIG. 1D).

Thereafter, a penile subcutaneous tissue 12 extending from the first circumferential incision 10 to the coronary sulcus, is released from the Buck's fascia 1 to form a space. The autologous graft from the penis is turned at an angle of 90 degrees and implanted into the space between the coronary sulcus and the first circumferential incision 10.

Afterwards, the implant is fixed to the Buck's fascia 1 and then surrounded with the penile skin and subcutaneous tissue of the distal end of the penis.

Finally, the implant is sutured to the incised sides and the circumferential incisions (FIG. 1E), thereby widening the penis.

In accordance with the present invention, the implant useful in the present invention is an autologous foreskin and subcutaneous tissue left after circumcision. Greater penis enlargement may be accomplished when a xenogenic or allogenic dermal tissue or an artificial implant is additionally recruited. In one preferred embodiment of the present invention, the implant may be the subcutaneous tissue 12 prepared by removing the epidermis and the dermis following isolation of the skin layer 11 and subcutaneous tissue 12 with a width of 1.0-1.5 cm from a distal end of the foreskin tissue to be applied to a distal end of the penis, said foreskin tissue being separated from the Buck's fascia 1 (FIG. 3).

In another preferred embodiment of the present invention, the implant to be sutured to the incised sides and the circumferential incisions is subcutaneous tissue 12 prepared by isolating penile skin 11 and subcutaneous tissue 12, as a graft with a width of 0.5~1.0 cm, from an end portion of the foreskin tissues to be moved from the penile foreskin tissues onto the sutured region, and then by removing the epidermis and dermis layers from the graft, said penile foreskin tissue being isolated from the Buck's fascia 1 of the penile body (FIG. 4).

There are a variety of variations in the implant. So long as it is an autograft obtained by circumcision, any of the variations may be used in the present invention. It will be appreciated that variations in proportions and alternatives in elements of the components shown will be apparent to those skilled in the art and are within the scope of embodiments of the present invention.

Example 2

The same procedure as in Example 1 is repeated with the exception that the implant is subcutaneous tissue 12 prepared by removing a part of the epidermis and dermis layer following isolation of the skin layer 11 and subcutaneous tissue 12 with a width of 0.5-1.0 cm from a distal end of the foreskin tissue to be applied to a distal end of the penis, said foreskin tissue being separated from the Buck's fascia 1.

Example 3

The same procedure as in Example 1 is repeated with the exception that the implant has a pattern of slits formed thereon. In one embodiment, the slits may be in the form of "x" or "-" (FIG. 5).

Although the invention has been illustrated and described with respect to one or more implementations, equivalent alterations and modifications will occur to others skilled in the art upon the reading and understanding of this specification and the attached drawings. In addition, while a particular feature of the invention may have been disclosed in only one of several implementations, such a feature may be combined with one or more other features of the other implementations as may be desired and as is advantageous for any given or particular application.

What is claimed is:

1. A method of complex phalloplasty using a circumcised foreskin and subcutaneous tissue as an autograft or implant, comprising:
   (i) making a first circumferential incision (10) on a penile skin (11) and subcutaneous tissue (12) on a periphery of a distal portion of a penile body;
   (ii) making a second circumferential incision (20) on the penile skin (11) and subcutaneous tissue (12) on the periphery of a middle portion of the penile body;
   (iii) incising a ventral part of the penis in an axial direction between the first circumferential incision (10) and the second circumferential incision (20);
   (iv) isolating from Buck's fascia (1) an area of the penile skin (11) and subcutaneous tissue (12) stretching from the ventral central part to a dorsal part to form an autograft or implant;
   (v) incising a central dorsal part of the penis to a depth of a subcutaneous tissue from the second incision line toward a proximal root of the penis;
   (vi) unfolding the penile subcutaneous tissues from Buck's fascia (1) to form a space in which to insert the autograft or implant;
   (vii) releasing from the Buck's fascia (1) a penile subcutaneous tissue extending from the first circumferential incision (10) to a coronary sulcus to form a space;
   (viii) turning the autograft or implant formed from the penile skin (11) and subcutaneous tissue (12) and released from the Buck's fascia (1) at an angle of 90 degrees;
   (ix) implanting the autograft or implant formed from the penile skin (11) and subcutaneous tissue (12) into the space between a coronary sulcus and the first circumferential incision (10);
   (x) fixing the autograft or implant onto the Buck's fascia (1);
   (xi) surrounding and covering the autograft or implant with the penile skin and subcutaneous tissue of the distal end of the penis; and
   (xii) suturing the autograft or implant to the incised sides and the circumferential incisions, whereby the penis can be enlarged and widened.

2. The method of claim 1, further comprising creating a graft from the subcutaneous tissue (12) autograft or implant prepared by isolating the penile skin (11) and subcutaneous tissue (12) from a distal end of a penile foreskin tissue, the graft with a width of 1.0-1.5 cm, and removing the epidermis and the dermis layer from the graft to be moved from the penile foreskin tissue on the Buck's fascia (1) to a penile end portion.

3. The method of claim 2, wherein the autograft or implant is patterned with multiple slits formed thereon.

4. The method of claim 1, further comprising creating a graft from the subcutaneous tissue (12) autograft or implant wherein the implant to be sutured to the incised sides and the circumferential incisions is a subcutaneous tissue (12) prepared by isolating a penile skin (11) and subcutaneous tissue (12), the graft with a width of 0.5-1.0 cm, from an end portion of the foreskin tissues to be moved from the penile foreskin tissues onto the sutured region, and then by removing epidermis and dermis layers from the graft, said penile foreskin tissue being isolated from the Buck's fascia (1) of the penile body.

5. The method of claim 1, wherein the autograft or implant is patterned with multiple slits formed thereon.

* * * * *